United States Patent [19]

Yukawa et al.

[11] Patent Number: 4,820,861

[45] Date of Patent: Apr. 11, 1989

[54] PROCESS FOR THE PRODUCTION OF N-FORMYL-ALPHA-L-ASPARTYL-L-PHENYLALANINE METHYL ESTER

[75] Inventors: Toshihide Yukawa; Haruo Kawasaki; Masao Nakamura, all of Kawasaki; Takashi Yamashita; Toshiaki Tsuji, both of Yokkaichi, all of Japan

[73] Assignee: Ajinomoto Co., Inc., Tokyo, Japan

[21] Appl. No.: 931,123

[22] Filed: Nov. 17, 1986

[30] Foreign Application Priority Data

Dec. 24, 1985 [JP] Japan ................................ 60-291180

[51] Int. Cl.⁴ .......................................... C07C 101/02
[52] U.S. Cl. ..................................................... 560/41
[58] Field of Search ........................... 560/41; 530/801

[56] References Cited

U.S. PATENT DOCUMENTS

| | | | |
|---|---|---|---|
| 3,833,553 | 9/1974 | Ariyoshi et al. | 560/41 |
| 3,901,871 | 8/1975 | Anderson | 560/41 |
| 3,933,781 | 1/1976 | Bachman et al. | 560/41 |
| 4,071,511 | 1/1978 | Takemoto et al. | 530/335 |
| 4,656,304 | 4/1987 | Oppici et al. | 560/41 |

*Primary Examiner*—Bruce D. Gray
*Attorney, Agent, or Firm*—Oblon, Fisher, Spivak, McClelland & Maier

[57] ABSTRACT

N-formyl-α-L-aspartyl-L-phenylalanine methyl ester is obtained by reacting L-phenylalanine methyl ester with N-formyl-L-aspartic acid anhydride in a reaction solvent containing acetic acid or acetic acid and formic acid in a complete mixing type continuous reaction mode.

3 Claims, 1 Drawing Sheet

PROCESS FOR THE PRODUCTION OF N-FORMYL-ALPHA-L-ASPARTYL-L-PHENYLALANINE METHYL ESTER

BACKGROUND OF THE INVENTION

α-L-Aspartyl-L-phenylalanine methyl ester (hereinafter referred to as α-APM) is known as an excellent sweetening agent, and as a process for its production, a process is known which comprises subjecting N-formyl-L-aspartic acid anhydride and PM to a condensation reaction in an organic solvent to form N-formyl-α-L-aspartyl-L-phenylalanine methyl ester (hereinafter referred to as For-α-APM) and then removing the formyl group from this reaction product to obtain the desired α-APM. See G.B. No. 2153365A.

However, in the production examples heretofore known, the desired For-α-APM is not the sole product but, in addition thereto, its isomer, N-formyl-β-L-aspartyl-L-phenylalanine methyl ester (hereinafter referred to as For-β-APM) is also by-produced, and the ratios of For-α-APM to For-β-APM (hereinafter referred to as the α/β ratio) are not always satisfactory, because, even when the practical concentrations of the reactants according to G.B. No. 2153365A (0.2~0.8 M/l) are employed, the α/β ratios are small (α/β ratio=1.8-3.3), and therefore it could not be regarded as an efficient production process. Indeed, when low concentrations of the reactants according to G.B. No. 2153365A (0.02 M/l) are employed, a considerably high α/β ratio of 5.5 is attained, but large reaction vessels are needed therefor. Large reaction vessels are not practical from the industrial point of view. On the contrary, according to the present invention, the α/β ratios can remarkably be enhanced at the practical concentrations of the reactants.

The by-production of For-β-APM reduces not only the yield of For-α-APM but also that of the end product, α-APM, and also this means the contamination of β-L-aspartyl-L-phenylalanine methyl ester (hereinafter referred to as β-APM) into α-APM, but since β-APM does not exhibit sweetness, α-APM contaminated with β-APM must be purified to remove the β-APM. Therefore, as described above, an increase in the α/β ratio is believed very advantageous in view that the desired end product α-APM may be obtained in a good yield.

SUMMARY OF THE INVENTION

The present inventors have been intensively studying in order to overcome such a disadvantage and, as a result, have come to surprisingly discover that by reacting N-formyl-L-aspartic acid anhydride and PM in a reaction medium in the presence of acetic acid or a mixture of acetic acid and formic acid in a complete mixing type continuous reaction mode, the desired α/β ratio is greatly enhanced, and therefore have accomplished this invention.

DETAILED DESCRIPTION OF THE DRAWING

Figure 1:
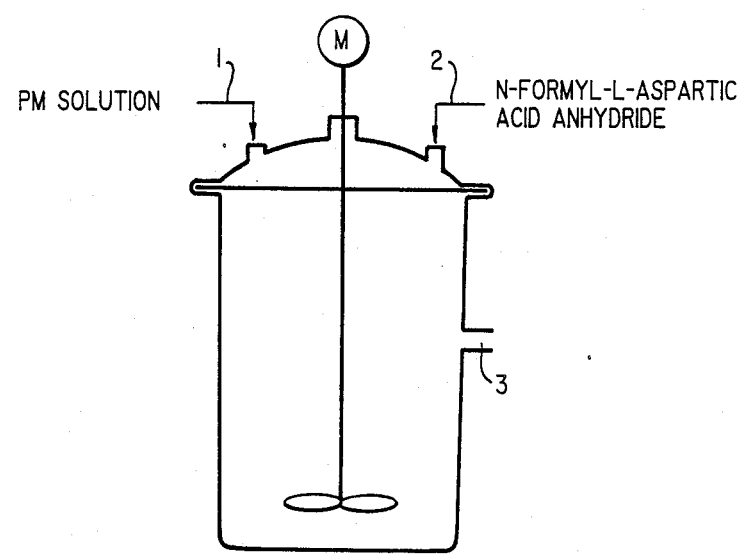
FIG. 1 is an example of a reactor for use in practicing the invention.

In FIG. 1 M is a motor adapted to rotate the stirrer in the reactor. A PM solution inlet 1, a N-formyl-L-aspartic acid anhydride inlet 2 and an overflow 3 are provided in the reactor.

In operation, a PM solution is continuously introduced via inlet 1, N-formyl-L-aspartic acid anhydride is continuously introduced via inlet 2 while the reaction mixture is stirred and continuously withdrawn by overflowing via overflow 3. The PM solution also contains the reaction solvent and acetic acid or acetic acid and formic acid.

DETAILED DESCRIPTION OF THE INVENTION

It is known that N-formyl-L-aspartic acid anhydride used in the process of this invention may be obtained by acting formic acid and acetic anhydride upon L-aspartic acid.

The reaction solvent used in the process of this invention may be any solvent as long as it is not particularly active upon the reactants and the reaction product. Representative examples thereof include hydrocarbons such as toluene, xylene, hexane etc., esters such as ethyl acetate, methyl propionate etc., carboxylic acids such as acetic acid, propionic acid etc., ketones such as acetone, methyl ethyl ketone etc., halogenated hydrocarbons such as chloroform, dichloromethane, ethylene dichloride etc., ethers such as diethyl ether, tetrahydrofuran, dioxane etc., as well as amides such as dimethylformamide etc., dimethylsulfoxide, water etc., and it is also possible to use a mixed solvent comprising any two or more of these.

PM may be obtained by methyl esterifying L-phenylalanine in the presence of an acid catalyst, and in general, it is obtained as an addition salt with said acid, and therefore by neutralizing and subsequently extracting with the above-mentioned organic solvent, it may be directly used in the reaction. Although the concentration of PM is not particularly restricted, 0.1-0.8 M/l is suitably employed.

On the other hand, N-formyl-L-aspartic acid anhydride may be used in the reaction as it is or may be dissolved or suspended in the aforesaid solvent after adding acetic acid or acetic acid and formic acid and used in the reaction. While the concentration thereof is not particularly restricted, 0.2-4 M/l is suitably used.

The amount of the acetic acid or acetic acid and formic acid to be used in the process of this invention may preferably be as high as possible in view of the dissolution of N-formyl-L-aspartic acid anhydride, but if too high, the α/β ratio is lowered, and therefore 10-150% (by weight) based on the reaction solvent is suitably employed. Where used in combination with acetic acid, the formic acid is suitably used in an amount of not greater than 30% (by weight) based on the acetic acid and not greater than 5% (by weight) based on the reaction solvent.

While the molar ratio of N-formyl-L-aspartic acid anhydride to PM used in the process of this invention is not particularly restricted, 0.5-5.0 is suitably employed. The reaction temperature is suitably not higher than 100° C., preferably not higher than 80° C., so as to prevent the racemization of the product.

While there is no particular restriction on the reaction time, the reaction rate between N-formyl-L-aspartic acid anhydride and L-phenylalanine methyl ester is great and thus it is not necessary to conduct the reaction for a prolonged time, and, although it depends on the reaction temperature, a retention time of within 6 hours is generally satisfactory. Further, it is also possible to conduct the reaction in a plurality of vessels by dividing into several stages (cascade mode).

By this invention, since it is possible to greatly enhance the α/β ratio and also greatly improve the yield of the desired end product, α-APM and also since the reaction is conducted in a continuous mode, it is efficient also in view of its device and thus it is extremely advantageous from an industrial point of view.

The following examples will be given to further describe this invention, but it should be noted that the embodiments of this invention are not restricted thereto.

EXAMPLE 1

To a reactor having an effective capacity of 800 ml shown in FIG. 1 were continuously fed a solution of PM in acetic acid—toluene (acetic acid:toluene=40:100) adjusted to a concentration of 0.5 M/l at a rate of 400 ml/hr and N-formyl-L-aspartic acid anhydride at a rate of 28.6 g/hr, while the mass in the reactor was completely being mixed with stirring, and the reaction mixture was continuously withdrawn by overflowing. During that time, the temperature of the reaction mixture was maintained at 30° C. The retention time for PM and N-formyl-L-aspartic acid anhydride was 120 minutes.

For-α-APM and For-β-APM in the reaction mixture withdrawn by overflowing were quantitatively determined by HPLC, and their ratio was determined to obtain an α/β ratio of 6.0.

EXAMPLE 2

To a reactor having an effective capacity of 800 ml shown in FIG. 1 were continuously fed a solution of PM in acetic acid—formic acid—toluene (acetic acid:formic acid:toluene=25:5:100) adjusted to a concentration of 0.5 M/l at a rate of 400 ml/hr and N-formyl-L-aspartic acid anhydride at a rate of 28.6 g/hr, while the mass in the reactor was completely being mixed and reacted with stirring, and the reaction mixture was continuously withdrawn by overflowing. During that time, the temperature of the reaction mixture was maintained at 30° C. The retention time for PM and N-formyl-L-aspartic acid anhydride was 120 minutes.

For-α-APM and For-β-APM in the reaction mixture withdrawn by overflowing were quantitatively determined by HPLC, and their ratio was determined to obtain an α/β ratio of 5.7.

EXAMPLE 3

To a reactor having an effective capacity of 800 ml shown in FIG. 1 were continuously fed a solution of PM in acetic acid—toluene (acetic acid:toluene=100:100) adjusted to a concentration of 0.5 M/l at a rate of 400 ml/hr and N-formyl-L-aspartic acid anhydride at a rate of 28.6 g/hr, while the mass in the reactor was completely being mixed with stirring, and the reaction mixture was continuously withdrawn by overflowing. During that time, the temperature of the reaction mixture was maintained at 15° C. The retention time for PM and N-formyl-L-aspartic acid anhydride was 120 minutes.

For-α-APM and For-β-APM in the reaction mixture withdrawn by overflowing were quantitatively determined by HPLC, and their ratio was determined to obtain an α/β ratio of 7.0.

EXAMPLE 4

To a reactor having an effective capacity of 800 ml shown in FIG. 1 were continuously fed a solution of PM in acetic acid—toluene (acetic acid:toluene=20:100) adjusted to a concentration of 0.5 M/l at a rate of 800 ml/hr and N-formyl-L-aspartic acid anhydride at a rate of 57.2 g/hr, while the mass in the reactor was completely being mixed with stirring, and the reaction mixture was continuously withdrawn by overflowing. During that time, the temperature of the reaction mixture was maintained at 30° C. The retention time for PM and N-formyl-L-aspartic acid anhydride was 60 minutes.

For-α-APM and For-β-APM in the reaction mixture withdrawn by overflowing were quantitatively determined by HPLC, and their ratio was determined to obtain an α/β ratio of 5.7.

EXAMPLE 5

To a reactor having an effective capacity of 800 ml shown in FIG. 1 were continuously fed a solution of PM in acetic acid—toluene (acetic acid:toluene=40:100) adjusted to a concentration of 0.2 M/l at a rate of 400 ml/hr and N-formyl-L-aspartic acid anhydride at a rate of 11.4 g/hr, while the mass in the reactor was completely being mixed with stirring, and the reaction mixture was continuously withdrawn by overflowing. During that time, the temperature of the reaction mixture was maintained at 30° C. The retention time for PM and N-formyl-L-aspartic acid anhydride was 120 minutes.

For-α-APM and For-β-APM in the reaction mixture withdrawn by overflowing were quantitatively determined by HPLC, and their ratio was determined to obtain an α/β ratio of 5.7.

EXAMPLE 6

To a reactor having an effective capacity of 800 ml shown in FIG. 1 were continuously fed a solution of PM in acetic acid—butyl acetate (acetic acid:butyl acetate=40:100) adjusted to a concentration of 0.4 M/l at a rate of 400 ml/hr and N-formyl-L-aspartic acid anhydride at a rate of 22.9 g/hr, while the mass in the reactor was completely being mixed with stirring, and the reaction mixture was continuously withdrawn by overflowing. During that time, the temperature of the reaction mixture was maintained at 30° C. The retention time for PM and N-formyl-L-aspartic acid anhydride was 120 minutes.

For-α-APM and For-β-APM in the reaction mixture withdrawn by overflowing were quantitatively determined by HPLC, and their ratio was determined to obtain an α/β ratio of 5.7.

COMPARATIVE EXAMPLE 1

To a reactor having an effective capacity of 800 ml shown in FIG. 1 were continuously fed a solution of PM in toluene adjusted to a concentration of 0.5 M/l at a rate of 400 ml/hr and N-formyl-L-aspartic acid anhydride at a rate of 28.6 g/hr, while the mass in the reactor was completely being mixed with stirring, and the reaction mixture was continuously withdrawn by overflowing. During that time, the temperature of the reaction mixture was maintained at 30° C. The retention time for PM and N-formyl-L-aspartic acid anhydride was 120 minutes.

For-α-APM and For-β-APM in the reaction mixture withdrawn by overflowing were quantitatively determined by HPLC, and their ratio was determined to obtain an α/β ratio of 0.9.

COMPARATIVE EXAMPLE 2

To a reactor having an effective capacity of 800 ml shown in FIG. 1 were continuously fed a solution of PM in acetic acid—toluene (acetic acid:toluene=5:100) adjusted to a concentration of 0.5 M/l at a rate of 400 ml/hr and N-formyl-L-aspartic acid anhydride at a rate of 28.6 g/hr, while the mass in the reactor was completely being mixed with stirring, and the reaction mixture was continuously withdrawn by overflowing. During that time, the temperature of the reaction mixture was maintained at 30° C. The retention time for PM and N-formyl-L-aspartic acid anhydride was 120 minutes.

For-$\alpha$-APM and For-$\beta$-APM in the reaction mixture withdrawn by overflowing were quantitatively determined by HPLC, and their ratio was determined to obtain an $\alpha/\beta$ ratio of 3.7.

COMPARATIVE EXAMPLE 3

To a reactor having an effective capacity of 800 ml shown in FIG. 1 were continuously fed a solution of PM in acetic acid—toluene (acetic acid:toluene=900:100) adjusted to a concentration of 0.5 M/l at a rate of 400 ml/hr and N-formyl-L-aspartic acid anhydride at a rate of 28.6 g/hr, while the mass in the reactor was completely being mixed with stirring, and the reaction mixture was continuously withdrawn by overflowing. During that time, the temperature of the reaction mixture was maintained at 30° C. The retention time for PM and N-formyl-L-aspartic acid anhydride was 120 minutes.

For-$\alpha$-APM and For-$\beta$-APM in the reaction mixture withdrawn by overflowing were quantitatively determined by HPLC, and their ratio was determined to obtain an $\alpha/\beta$ ratio of 4.3.

COMPARATIVE EXAMPLE 4

(Example of a Batch Reaction)

7.2 g of an N-formyl-L-aspartic acid anhydride was added to 100 ml of a solution of PM in acetic acid—toluene (acetic acid:toluene=40:100) adjusted to a concentration of 0.5 M/l, and stirred at 30° C. for 2 hours.

For-$\alpha$-APM and For-$\beta$-APM in the reaction mixture were quantitatively determined by HPLC, and their ratio was determined to obtain an $\alpha/\beta$ ratio of 3.5.

We claim:

1. In the process for the production of N-formyl-$\alpha$-L-apartyl-L-phenylalanine methyl ester by the reaction of N-formyl-L-aspartic acid anhydride with L-phenylalanine methyl ester the improvement comprising carrying out said reaction in a reaction solvent other than acetic acid and in the presence of acetic acid or acetic acid and formic acid, the amount of acetic acid or acetic acid and formic acid present being 10-150% by weight based on the reaction solvent, in a complete mixing type continuous reaction mode.

2. The process according to claim 1 wherein the reaction solvent is toluene or ethyl acetate.

3. The process according to claim 1, wherein the amount of acetic acid present is from 20-150% by weight based on the reaction solvent.

* * * * *